United States Patent [19]

Ojima et al.

[11] 4,352,752

[45] Oct. 5, 1982

[54] PROCESS FOR THE PREPARATION OF DIPEPTIDES

[75] Inventors: Iwao Ojima, Sagamihara; Shigemi Suga, Oiso, both of Japan

[73] Assignee: Sagami Chemical Research Center, Tokyo, Japan

[21] Appl. No.: 240,983

[22] Filed: Mar. 5, 1981

[30] Foreign Application Priority Data

Mar. 7, 1980 [JP] Japan .................................. 55-28060

[51] Int. Cl.³ ................. C07C 103/52; C07C 101/30; C07C 101/72
[52] U.S. Cl. .............................. 260/112.5 R; 560/39; 562/444
[58] Field of Search ................. 260/112.5 R; 560/39; 562/444

[56] References Cited

PUBLICATIONS

Manhas et al., Natural and Synthetic Part 1, Annex 1 pp. 79–86.

*Primary Examiner*—Delbert R. Phillips
*Attorney, Agent, or Firm*—Schwartz, Jeffery, Schwaab, Mack, Blumenthal & Koch

[57] ABSTRACT

There is provided a novel process for the preparation of a dipeptide represented by the formula:

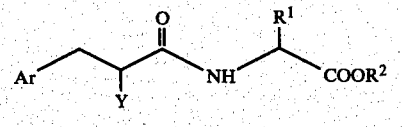

wherein Ar represents an aromatic group; $R^1$ represents a hydrogen atom, an alkyl group or an aryl group; $R^2$ represents a hydrogen atom, an alkyl group or an aromatic group; Y represents a hydroxy group, an amino group or an acylamino group, which comprises subjecting a β-lactam compound represented by the formula:

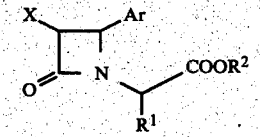

wherein Ar, $R^1$ and $R^2$ have the same meanings as defined above, and X represents a hydroxy group, an amino group or an acylamino group, an azido group or a benzyloxy group, to hydrogenolysis in the presence of a catalyst. The process can be practiced without any complicated procedure as seen in the conventional processes for the preparation of peptides.

13 Claims, No Drawings

PROCESS FOR THE PREPARATION OF DIPEPTIDES

BACKGROUND OF THE INVENTION

This invention relates to a process for the preparation of a dipeptide derivative. More particularly, it relates to a process for the preparation of a dipeptide derivative by hydrogenolysis of a lactam compound in the presence of a catalyst.

Recently, peptides having physiological activities have successively been discovered so that various methods for preparing such peptides have extensively been developed.

Conventionally, peptides have been prepared by (i) DCC (dicyclohexyl carbodiimide) Method (E. Gross and J. Meienhofer, "The Peptides", Vol. 1, p. 241–261, Academic Press, N.Y. (1979)); (ii) Activated Ester Method (Idem. ibid., p. 105 (1960)); (iii) Enzyme Method (Y. Isowa, M. Ohmori, M. Sato and K. Mori, Bull. Chem. Soc. Japan, 50, 2766 (1977)); and so on.

However, these methods have the problem to be solved that the procedures for isolation and purification of the desired product are rather complicated.

As a result of the extensive studies upon the processes for the preparation of dipeptides, which are entirely different from the conventional ones, the present inventors have found a novel process by which the desired dipeptide can be obtained from a readily available starting material without any complicated procedure, and accomplished the present invention.

SUMMARY OF THE INVENTION

An object of this invention is to provide a process for the preparation of dipeptides which is more advantageous as compared with the conventional ones.

The process according to this invention comprises subjecting a $\beta$-lactam compound represented by the following formula (I):

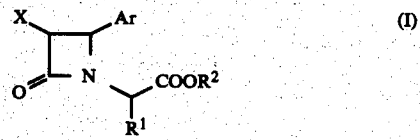

wherein Ar represents an aromatic group; $R^1$ represents a hydrogen atom, an alkyl group or an aromatic group; $R^2$ represents a hydrogen atom, an alkyl group or an aromatic group; and X represents a hydroxy group, an amino group, an acylamino group, an azido group or a benzyloxy group, to hydrogenolysis in the presence of a catalyst to prepare a dipeptide derivative represented by the formula (II):

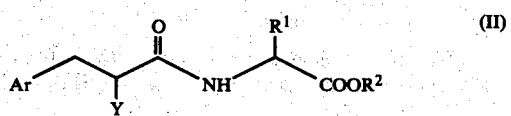

wherein Ar, $R^1$ and $R^2$ have the same meanings as defined above; and Y represents a hydroxy group, an amino group or an acylamino group.

The aromatic group represented by Ar in the above formulae (I) and (II) includes, for example, phenyl, naphthyl, pyridyl, pyrrolyl, furyl, indolyl or imidazolyl group, which groups may be substituted by halogen or amino, acylamino, alkyl, aryl, hydroxy, alkoxy, aryloxy, acyloxy, carboxyl, ester, nitro, imino or imido group.

The alkyl group represented by $R^1$ or $R^2$ includes, for example, methyl, ethyl, propyl, isopropyl, butyl, isobutyl, sec-butyl or tert-butyl group, which groups may be substituted by halogen or amino, acylamino, alkyl, aryl, hydroxy, alkoxy, aryloxy, acyloxy, carboxyl, ester, nitro, imino or imido group.

The aromatic group represented by $R^1$ or $R^2$ includes, for example, phenyl, naphthyl, pyridyl, pyrrolyl, furyl, indolyl or imidazolyl group, which groups may be substituted by halogen or amino, acylamino, aryl, hydroxy, alkoxy, aryloxy, acyloxy, carboxyl, ester, nitro, imino or imido group.

The acylamino group represented by X or Y includes, for example, acetylamino, azidoacetylamino, chloroacetylamino, trichloroacetylamino, trifluoroacetylamino, benzylamino, t-butoxycarbonylamino, benzyloxycarbonylamino or p-nitrobenzyloxycarbonylamino group.

DETAILED DESCRIPTION OF PREFERRED EMBODIMENTS

The $\beta$-lactam compound of the above formula (I) which is used as a starting material in the present process can readily be obtained by reacting a Schiff base which is obtained almost quantitatively from a corresponding aldehyde and a corresponding $\alpha$-amino acid ester, with azidoacetyl chloride or a benzyloxyacetyl chloride (See Referential examples as shown hereinafter).

The $\beta$-lactam compound includes, for example,
1-(1-Methoxycarbonylbenzyl)-3-azido-4-phenylazetidin-2-one,
1-(1-Ethoxycarbonylbenzyl)-3-amino-4-phenylazetidin-2-one,
1-(1-Ethoxycarbonylbenzyl)-3-acetylamino-4-phenylazetidin-2-one,
1-(1-Methoxycarbonylbenzyl)-3-benzyloxy-4-phenylazetidin-2-one,
1-(1-Methoxycarbonylbenzyl)-3-hydroxy-4-phenylazetidin-2-one,
1-(1-Methoxycarbonyl-2-methylpropyl)-3-azido-4-phenylazetidin-2-one,
1-(1-Ethoxycarbonyl-2-methylpropyl)-3-amino-4-phenylazetidin-2-one,
1-(1-Methoxycarbonyl-2-methylpropyl)-3-acetylamino-4-phenylazetidin-2-one,
1-(1-Ethoxycarbonyl-2-methylpropyl)-3-benzyloxy-4-phenylazetidin-2-one,
1-(1-Methoxycarbonyl-2-methylpropyl)-3-hydroxy-4-phenylazetidin-2-one,
1-(1-Methoxycarbonylethyl)-3-azido-4-phenylazetidin-2-one,
1-(1-Methoxycarbonylethyl)-3-amino-4-phenylazetidin-2-one,
1-(1-Ethoxycarbonyl)-3-acetylamino-4-phenylazetidin-2-one,
1-(1-Methoxycarbonylethyl)-3-benzyloxy-4-phenylazetidin-2-one,
1-(1-Methoxycarbonylethyl)-3-hydroxy-4-phenylazetidin-2-one,
1-(1-Methoxycarbonyl-2-phenylethyl)-3-azido-4-phenylazetidin-2-one,
1-(1-Methoxycarbonyl-2-phenylethyl)-3-amino-4-phenylazetidin-2-one, 1-(1-Methoxycarbonyl-2-phenylethyl)-3-acetylamino-4-phenylazetidin-2-one,
1-(1-Methoxycarbonyl-2-phenylethyl)-3-benzyloxy-4-phenylazetidin-2-one,
1-(1-Methoxycarbonyl-2-phenylethyl)-3-hydroxy-4-phenylazetidin-2-one,
1-(1-Methoxycarbonyl-3-methylthiopropyl)-3-azido-4-phenylazetidin-2-one,
1-(1-Methoxycarbonyl-3-methylthiopropyl)-3-amino-4-phenylazetidin-2-one,
1-(1-Methoxycarbonyl-3-methylthiopropyl)-3-acetylamino-4-phenylazetidin-2-one,
1-(1-Methoxycarbonyl-3-methylthiopropyl)-3-benzyloxy-4-phenylazetidin-2-one,
1-(1-Ethoxycarbonyl-3-methylthiopropyl)-3-hydroxy-4-phenylazetidin-2-one,
1-(1-Methoxycarbonylbenzyl)-3-azido-4-(p-benzyloxycarbonyloxyphenyl)azetidin-2-one,
1-(1-Methoxycarbonylbenzyl)-3-azido-4-(3,4-dibenzyloxyphenyl)azetidin-2-one,
1-(1-Methoxycarbonyl-2-methylpropyl)-3-amino-4-(p-benzyloxyphenyl)azetidin-2-one,
1-Ethoxycarbonylmethyl-3-azido-4-phenylazetidin-2-one,
1-(1-Methoxycarbonylethyl)-3-azido-4-(3,4-bisbenzyloxycarbonyloxyphenyl)azetidin-2-one,
1-Methoxycarbonylmethyl-3-azido-4-(p-t-butoxycarbonyloxyphenyl)-azetidin-2-one,
1-(Methoxycarbonyl-p-benzyloxyphenylmethyl)-3-azido-4-phenylazetidin-2-one,
1-(1-t- Butoxycarbonylethyl)-3-azido-4-phenylazetidin-2-one,
1-(1-t-Butoxycarbonylmethyl)-3-amino-4-(p-benzyloxyphenyl)azetidin-2-one,
1-(1-Benzyloxycarbonyl-2-phenylethyl)-3-azido-4-phenylazetidin-2-one
and
1-(1-Benzyloxycarbonyl-2-methylpropyl)-3-trifluoroacetylamino-4-(p-benzyloxycarbonyloxyphenyl)azetidin-2-one.

As the catalyst to be used for the process according to this invention, there may be mentioned a palladium catalyst, such as Pd Black (palladium black), Pd-C (palladium on carbon), palladium hydroxide (Pd(OH)$_2$), palladium oxide (PdO) and palladium chloride (PdCl$_2$); a nickel catalyst such as Raney Nickel; and so on. Among these catalysts, a palladium catalyst is preferred since it enhances the yield of the desired product and is available at lower cost.

The amount of the catalyst to be used, while it depends on the hydrogen pressure and the reaction temperature, usually ranges from 0.1 to 100 mole %, preferably from 1 to 50 mole % in terms of the palladium atom, based on the starting β-lactam compound.

In practicing the process according to this invention, it is preferable to use a solvent. As the solvent, there may be employed wide varieties of solvents, for example, alcohols such as methanol and ethanol; halogenated hydrocarbons such as methylene chloride and chloroform; aromatic hydrocarbons such as benzene and toluene; ethers such as tetrahydrofuran; aprotic polar solvents such as acetonitrile and dimethylformamide.

The reaction is carried out usually at 0° to 150° C., preferably at room temperature to 100° C. in view of the reaction efficiency as well as the ease of the reaction procedure.

The present invention will further be explained in more detail by way of the following Referential examples and Examples, which however should not be construed to limit the present invention.

REFERENTIAL EXAMPLE 1

After an ammonia gas was blown into 400 ml. of a solution of 20 g. of methyl D-phenylglycinate hydrochloride in chloroform at room temperature for 30 minutes, the formed ammonium chloride was filtered off and the resulting filtrate was concentrated under reduced pressure to give 30 g. of a solution of methyl D-phenylglycinate in chloroform. To the thus obtained solution was added 180 ml. of benzene, and 180 ml. of a solution of 9.57 g. of benzaldehyde in benzene was further added dropwise thereto under ice-cooling over 15 minutes. After 50 g. of anhydrous sodium sulfate was added thereto, the mixture was stirred at room temperature for 12 hours. The resulting insoluble substance was filtered off by using a glass fiber No. G3, and the obtained filtrate was concentrated under reduced pressure to give 25 g. of white crystals. The thus obtained crystals were recrystallized from n-hexane to give 21.0 g. (yield: 83.6%) of N-benzylidene-1-methoxycarbonylbenzylamine as white crystals, which showed a melting point of 86.0° to 89.0° C.

NMR (CDCl$_3$): δ 3.63 (singlet, 3H), 4.13 (singlet, 1H), 7.13–8.0 (multiplet, 10H), 8.37 (singlet, 1H).

IR (KBr disk: 1750 ($\nu_{C=O}$)cm$^{-1}$

REFERENTIAL EXAMPLE 2

To 50 ml. of a solution of 3.50 g. of D-N-benzylidene-1-methoxycarbonylbenzylamine and 2.80 g. of triethylamine in methylene chloride, there was gradually added dropwise 50 ml. of a solution of 3.31 g. of azidoacetyl chloride in methylene chloride at −78° C. After the dropwise addition, the resulting reaction mixture was stirred at room temperature for 12 hours and then washed with water. After drying over anhydrous magnesium sulfate, the solvent was removed by distillation under reduced pressure to give 4.97 g. of a brown oily substance. According to analyses by NMR, IR and thin layer chromatography, it was revealed that the oily substance was a mixture of two kinds of diastereomers of 1-(1-methoxycarbonylbenzyl)-3-azido-4-phenylazetidin-2-one (Diastereomers A and B). The mixture was purified by silica gel chromatography with a short column to give 4.10 g. (yield: 88.4%) of an oily β-lactam. Further, the two diastereomers could be separated from each other by silica gel chromatography.

Diastereomer A

NMR (CDCl$_3$): δ 3.72 (singlet, 3H), 4.96 (doublet, 1H), 4.20 (doublet, 1H), 4.48 (singlet, 1H), 5.72–6.40 (multiplet, 10H).

IR (KBr): 2110 ($\nu_{N_3}$), 1765 ($\nu_{C=O}$), 1740 ($\nu_{C=O}$)cm$^{-1}$.

Diastereomer B

NMR (CDCl$_3$): δ 3.56 (singlet, 3H), 4.76 (doublet, 1H), 4.86 (doublet, 1H), 5.01 (singlet, 1H), 6.90–7.70 (multiplet, 10H).

IR (KBr): 2110 ($\nu_{N_3}$), 1765 ($\nu_{C=O}$), 1740 ($\nu_{C=O}$)cm$^{-1}$.

REFERENTIAL EXAMPLE 3

In a pyrex reactor (usual apparatus for hydrogenation under ambient pressure) which was connected with a gas burette, there was placed 79.0 mg. of a 10% Pd-C, and then the reaction system was substituted with hydrogen gas. Then, 30 ml. of an ethanolic solution of 1-(1-methoxycarbonylbenzyl)-3-azido-4-phenylazetidin-2-one, which had been obtained in Referential example 2, was added thereto, and hydrogenolysis was carried out with stirring at room temperature. The reaction was completed in 12 hours. The completion of the reaction was confirmed by the amount of absorbed hydrogen and by thin layer chromatography. After the catalyst was separated by filtration with a glass filter No. G4, the solvent was removed from the filtrate by distillation under reduced pressure by using a rotary evaporator to give 462 mg. of a yellow oil. The oil was purified by silica gel column chromatography to give 370 mg. (yield: 80.1%) of 1-(1-methoxycarbonylbenzyl)-3-amino-4-phenylazetidin-2-one as an oil.

NMR (CDCl$_3$): δ 1.24 (broad singlet, 2H), 3.71 (singlet, 3H), 4.52 (doublet, 1H), 5.15 (doublet, 1H), 5.60 (singlet, 1H), 6.74–7.74 (multiplet, 10H).

IR (KBr): 3400 ($\nu_{NH_2}$), 1790–1700 ($\nu_{C=O}$)cm$^{-1}$.

REFERENTIAL EXAMPLE 4

To 5 ml. of a solution of 280 mg. of 1-(1-methoxycarbonylbenzyl)-3-amino-4-phenylazetidin-2-one obtained in Referential example 3 and 100 mg. of triethylamine in chloroform, there was added dropwise under ice-cooling 78.0 mg. of acetyl chloride. After stirring at room temperature for 30 minutes, the reaction mixture was washed with water and dried over anhydrous magnesium sulfate, followed by evaporation of the solvent under reduced pressure to give 318 mg. (yield: 100%) of 1-(1-methoxycarbonylbenzyl)-3-acetylamino-4-phenylazetidin-2-one as an oil.

NMR (CDCl$_3$): δ 1.73 (singlet, 3H), 3.87 (singlet, 3H), 5.30 (doublet, 1H), 5.50 (singlet, 1H), 5.70 (doublet, 1H), 6.10 (broad doublet, 1H), 6.73–7.50 (multiplet, 10H).

IR (KBr): 3325 ($\nu_{NH}$), 1750 ($\nu_{C=O}$), 1650 (amide I), 1510 (amide II)cm$^{-1}$.

REFERENTIAL EXAMPLE 5

Under ice-cooling, 30 ml. of a solution of 5.02 g. of benzyloxyacetyl chloride in benzene was gradually added dropwise to 30 ml. of a solution of 4.00 g. of L-N-benzylidene-1-methoxycarbonyl-2-methylpropylamine and 2.75 g. of triethylamine in benzene. After the dropwise addition and stirring at room temperature for 12 hours, the reaction mixture was washed with water and dried over anhydrous magnesium sulfate, followed by removal of the solvent by distillation under reduced pressure to give 8.07 g. of a yellow oil. Analyses by NMR, IR and thin layer chromatography revealed that the oily substance was a mixture of two kinds of diastereomers of 1-(1-methoxycarbonylethyl)-3-benzyloxy-4-phenylazetidin-2-one (Diastereomers A and B). The substance was purified by short column chromatography (silica gel) to give 6.65 g. of a β-lactam as white crystals melting at 55.0° to 65.0° C. Further, the two diastereomers could be separated from each other by silica gel column chromatography.

Diastereomer A

M.P.: 79.0°–81.0° C.

NMR (CDCl$_3$): δ 1.11 (doublet, 3H), 3.68 (singlet, 3H), 4.17 (quartet, 2H), 4.56 (quartet, 1H), 4.90 (doublet, 1H), 5.00 (doublet, 1H), 6.80–7.60 (multiplet, 10H).

IR (KBr): 1760 ($\nu_{C=O}$)cm$^{-1}$.

Diastereomer B

M.P.: 84.0°–87.0° C.

NMR (CDCl$_3$): δ 1.59 (doublet, 3H), 3.56 (singlet, 3H), 4.19 (quartet, 2H), 4.78 (doublet, 1H), 4.86 (doublet, 1H), 6.80–7.60 (multiplet, 10H).

IR (KBr): 1760 ($\nu_{C=O}$)cm$^{-1}$.

REFERENTIAL EXAMPLE 6

After a 10% Pd-C (110 mg.) was placed in a pyrex reactor connected with a gas burette and the reaction system was substituted with hydrogen gas, 40 ml. of an ethanolic solution of Diastereomer A (700 mg.) of 1-(1-methoxycarbonylethyl)-3-benzyloxy-4-phenylazetidin-2-one obtained in Referential example 5 was introduced thereinto and hydrogenolysis was carried out with stirring at room temperature. The reaction was completed in 12 hours. The completion of the reaction was confirmed by the amount of the absorbed hydrogen and by thin layer chromatography. After the catalyst was removed by filtration from the reaction mixture through a glass fiber No. G4, the solvent was removed from the filtrate by distillation under reduced pressure by using a rotary evaporator to give 500 mg. of a colorless oil. The resulting oil was purified by column chromatography to give 470 mg. (yield: 91.6%) of 1-(1-methoxycarbonylethyl)-3-hydroxy-4-phenylazetidin-2-one as an oil.

NMR (CDCl$_3$): δ 1.16 (doublet, 3H), 3.56 (broad singlet, 1H), 3.70 (singlet, 3H), 4.54 (quartet, 1H), 5.01 (doublet, 1H), 5.10 (multiplet, 1H), 7.36 (singlet, 5H).

IR (KBr): 3400 ($\nu_{OH}$), 1750 ($\nu_{C=O}$)cm$^{-1}$.

REFERENTIAL EXAMPLE 7

To 75 ml. of a solution of N-benzylidene-1-(S)-t-butoxycarbonylethylamine (5.07 g., 21.7 mmol) and triethylamine (4.84 g., 47.8 mmol) in methylene chloride, there was gradually added dropwise 75 ml. of a solution of azidoacetyl chloride (5.19 g., 43.5 mmol) in methylene chloride at −78° C. After stirring at −78° C. to room temperature for 14 hours, the reaction mixture was washed with water and then with a saturated saline solution, followed by drying over anhydrous magnesium sulfate. After removal of the solvent by distillation, the residue was subjected to silica gel column chromatography, using hexane-ethyl acetate (3:1) as an eluent, to give 1-(1(S)-t-butoxycarbonylethyl)-3(S)-azido-4(R)-azetidin-2-one (2.68 g., yield: 39%) and 1-(1(S)-t-butoxycarbonylethyl)-3(R)-azido-4(S)-phenylazetidin-2-one (2.82 g., yield: 41%).

1-(1(S)-t-Butoxycarbonylethyl)-3(S)-azido-4(R)-phenylazetidin-2-one

M.P.: 53°–54° C.

$[\alpha]_D^{20}$: −122.6° (C=1.00, MeOH)

NMR (CDCl$_3$): δ 1.44 (singlet, 9H), 1.67 (doublet, 3H, J=7.5 Hz), 3.78 (quartet, 1H, J=7.5 Hz), 4.83 (doublet, 1H, J=5.5 Hz), 4.92 (doublet, 1H, J=5.5 Hz), 7.27–7.50 (multiplet, 5H).

IR (neat): 2120, 1770, 1740 cm$^{-1}$.

Elementary analysis (for C$_{16}$H$_{20}$N$_4$O$_3$): Calcd.: C, 60.75; H, 6.37; N, 17.71. Found: C, 60.72; H, 6.39; N, 17.64.

1-(1(S)-t-Butoxycarbonylethyl)-3(R)-azido-4(S)-phenylazetidin-2-one

M.P.: 95°–96° C.

$[\alpha]_D^{20}$: +125.6° (C=1.00, MeOH)

NMR (CDCl$_3$): δ 1.14 (doublet, 3H, J=7.5 Hz), 1.48 (singlet, 9H), 4.42 (quartet, 1H, J=7.5 Hz), 4.91 (doublet, 1H, J=5 Hz), 5.12 (doublet, 1H, J=5 Hz), 7.37 (singlet, 5H).

IR (neat): 2120, 1770, 1730 cm$^{-1}$.

Elementary analysis (for C$_{16}$H$_{20}$N$_4$O$_3$): Calcd.: C, 60.75; H, 6.37; N, 17.71. Found: C, 60.74; H, 6.34; N, 17.83.

REFERENTIAL EXAMPLE 8

Using N-benzylidene-1(S)-t-butoxycarbonyl-3-methylbutylamine (8.46 g., 30.7 mmol) as a starting material, the reaction, separation and purification were carried out under the same conditions as in Referential example 7 to give a mixture of 1-(1(S)-t-butoxycarbonyl-3-methylbutyl)-3(S)-azido-4(R)-phenylazedidin-2-one and 1-(1(S)-t-butoxycarbonyl-3-methylbutyl)-3(R)-azido-4(S)-phenylazetidin-2-one (9.18 g., yield: 83.4%).

NMR (CDCl$_3$): δ 0.51–1.07 (multiplet, Diastereomers A and B) (6H), [1.41 (singlet, Diastereomer A), 1.48 (singlet, Diastereomer B)] (9H), 1.14–2.56 (multiplet, Diastereomers A and B) (3H), 3.55–3.86, 4.05–4.36 (multiplet, Diastereomers A and B) (1H), [4.81 (singlet, Diastereomer B), 4.87 (doublet, J=5 Hz, Diastereomer A), 5.06 (doublet, J=5 Hz, Diastereomer A)] (2H), 7.20–7.42 (multiplet, Diastereomers A and B) (5H).

IR (neat): 2120, 1775, 1735 cm$^{-1}$.

REFERENTIAL EXAMPLE 9

Using N-(4-fluorobenzylidene)-1(S)-t-butoxycarbonyl-3-methylbutylamine (10.09 g., 34.4 mmol) as a starting material, the reaction, separation and purification were carried out under the same conditions as in Referential example 7 to give a mixture of 1-(1(S)-t-butoxycarbonyl-3-methylbutyl)-3(S)-azido-4(R)-(4-fluorophenyl)azetidin-2-one and 1-(1(S)-t-butoxycarbonyl-3-methylbutyl)-3(R)-azido-4(S)-(4-fluorophenyl)azetidin-2-one (12.51 g., yield: 96.6%).

NMR (CDCl$_3$): δ 0.53–1.07 (multiplet, Diastereomers A and B) (6H), [1.41 (singlet, Diastereomer A), 1.48 (singlet, Diastereomer B)] (9H), 1.07–2.56 (multiplet, Diastereomers A and B) (3H), 3.55–3.86, 4.05–4.36 (multiplet, Diastereomers A and B) (1H), [4.83 (singlet, Diastereomer B), 4.92 (doublet, J=5 Hz, Diastereomer A), 5.11 (doublet, J=5 Hz, Diastereomer A)] (2H), 6.95–7.50 (multiplet, Diastereomers A and B) (4H).

IR (neat): 2120, 1775, 1735 cm$^{-1}$.

REFERENTIAL EXAMPLE 10

Using N-benzylidene-1(S)-benzyloxycarbonyl-3-methylbutylamine (3.62 g., 11.7 mmol) as a starting material, the reaction, separation and purification were carried out under the same conditions as in Referential example 7 to give a mixture of 1-(1(S)-benzyloxycarbonyl-3-methylbutyl)-3(S)-azido-4(R)-phenylazetidin-2-one and 1-(1(S)-benzyloxycarbonyl-3-methylbutyl)-3(R)-azido-4(S)-phenylazetidin-2-one (3.55 g., yield: 77.3%).

NMR (CDCl$_3$): δ 0.51–1.07 (multiplet, Diastereomers A and B) (6H), 1.15–2.50 (multiplet, Diastereomers A and B) (3H), 3.75–4.06, 4.28–4.60 (multiplet, Diastereomers A and B) (1H), 4.77–5.10 (multiplet, Diastereomers A and B) (2H), [5.03 (singlet, Diastereomer A), 5.14 (singlet, Diastereomer B)] (2H), 7.06–7.52 (multiplet, Diastereomers A and B) (10H). IR (neat): 2120, 1775, 1740 cm$^{-1}$.

EXAMPLE 1

After a 10% Pd-C (100 mg.) was placed in a pyrex reactor connected with a gas burette and the reaction system was substituted with hydrogen gas, 30 ml. of an ethanolic solution of 1-(1-methoxycarbonylbenzyl)-3-acetylamino-4-phenylazetidin-2-one (318 mg.) obtained in Referential example 4 was added thereto, and hydrogenolysis was carried out at room temperature with stirring. The reaction was completed in 14 hours. The completion of the reaction was confirmed by checking the amount of the hydrogen gas absorbed and by thin layer chromatography. The catalyst was removed by fiteration using a glass filter No. G4 and the solvent was removed from the filtrate by distillation under reduced pressure by using a rotary evaporator to give 288 mg. (yield: 90.1%) of methyl ester of N-acetylphenyl alanyl-phenylglycine as white crystals melting at 177.0° to 180.0° C.

NMR (CDCl$_3$): δ 1.93 (singlet, 3H), 2.97 (doublet, 2H), 3.63 (singlet, 3H), 3.78 (quartet, 1H), 4.43 (doublet, 1H), 5.38 (broad doublet, 1H), 5.74–6.60 (multiplet, 10H).

IR (KBr disk): 3325 ($\nu_{NH}$), 3300 ($\nu_{NH}$), 1740 ($\nu_{C=O}$), 1640 (amide I), 1535 (amide II)cm$^{-1}$.

EXAMPLE 2

According to the same procedure as in Example 1, 1-(1-methoxycarbonyl-2-methylpropyl)-3-acetylamino-4-phenylazetidin-2-one (230 mg.) was subjected to hydrogenolysis at 50° C. in methanol (20 ml.) in the presence of a 10% Pd-C (310 mg.) under a hydrogen pressure of one atmosphere. The reaction was completed in 18 hours. The same after-treatment as in Example 1 was followed to give methyl ester of N-acetylphenylalanylvaline (220 mg., yield: 95.5%).

NMR (CDCl$_3$): δ 0.79 (multiplet, 6H) 1.93 (broad singlet, 3H), 3.02 (broad singlet, 2H), 3.66 (singlet, 3H), 4.38 (broad singlet, 1H), 4.80 (broad singlet, 1H), 6.72 (multiplet, 2H), 7.24 (multiplet, 5H).

IR (KBr disk): 3300 ($\nu_{NH}$), 1745 ($\nu_{C=O}$), 1640 (amide I), 1540 (amide II)cm$^{-1}$.

EXAMPLE 3

According to the same procedure as in Example 1, 1-(1-methoxycarbonyl-2-phenylethyl)-3-acetylamino-4-phenylazetidin-2-one (300 mg.) was subjected to hydrogenolysis at 50° C. in methanol (30 ml.) under a hydrogen pressure of one atmosphere in the presence of a 10% Pd-C (350 mg.). The reaction completed in 18 hours. The same after-treatment as in Example 1 was followed to give methyl ester of N-acetylphenylalanylalanine (280 mg., yield: 92.8%) melting at 128.0°–132.0° C.

NMR (CDCl$_3$): δ 1.87 (singlet, 3H), 2.96 (multiplet, 2H), [3.58 (singlet), 3.60 (singlet)] (3H), 4.52 (multiplet, 2H), 6.50 (broad triplet, 1H), 6.68 (broad doublet, 1H), 6.80–7.80 (multiplet, 10H).

IR (KBr disk): 3300 ($\nu_{NH}$), 1740 ($\nu_{C=O}$), 1650 (amide I), 1540 (amide II)cm$^{-1}$.

EXAMPLE 4

According to the same procedure as in Example 1, 1-(1-methoxycarbonylethyl)-3-acetylamino-4-phenylazetidin-2-one (400 mg.) was subjected to hydrogenolysis at 50° C. in ethanol (30 ml.) under a hydrogen pressure of one atmosphere in the presence of a 10% Pd-C (580 mg.). The reaction was completed in 7 hours.

The same after-treatment as in Example 1 was followed to give methyl ester of N-acetylphenylalanylalanine (390 mg., yield: 96.8%) melting at 147.0°–155.0° C.

NMR (CDCl$_3$): δ [1.20 (doublet), 1.33 (doublet)] (3H), 1.94 (singlet, 3H), 2.02 (broad doublet, 2H), 2.67 (singlet, 3H), 3.44 (broad triplet, 1H), 3.74 (broad quartet, 1H), 5.48–6.04 (multiplet, 2H), 6.04–6.06 (multiplet, 5H).

IR (KBr disk): 3300 ($v_{NH}$), 3225 ($v_{NH}$), 1760 ($v_{C=O}$), 1750 ($v_{C=O}$), 1640 (amide I), 1550 (amide II)cm$^{-1}$.

EXAMPLE 5

According to the same procedure as in Example 1, 1-(1-methoxycarbonyl-2-methylpropyl)-3-azido-4-phenylazetidin-2-one (500 mg.) was subjected to hydrogenolysis at 50° C. in ethanol (30 ml.) under a hydrogen pressure of one atmosphere in the presence of a 10% Pd-C (175 mg.). The reaction was completed in 19 hours. The same after-treatment as in Example 1 was followed to give methyl ester of phenylalanylvaline (378 mg., yield: 81.9%), which was an oil.

NMR (CDCl$_3$): δ [0.87 (doublet), 0.93 (doublet)] (6H), 1.44 (singlet, 2H), 2.60 (multiplet, 1H), 2.68 (multiplet, 1H), 3.26 (multiplet, 1H), 3.62 (multiplet, 1H), 3.70 (singlet, 3H), 4.49 (quartet, 1H), 7.25 (singlet, 5H), 7.75 (broad triplet, 1H).

IR (KBr): 3675–3200 ($v_{NH_2}$ and $v_{NH}$), 1740 ($v_{C=O}$), 1660 (amide I), 1500 (amide II)cm$^{-1}$.

EXAMPLE 6

According to the same procedure as in Example 1, 1-(methoxycarbonyl-2-methylpropyl)-3-amino-4-phenylazetidin-2-one (458 mg.) was subjected to hydrogenolysis at 50° C. in ethanol (30 ml.) under a hydrogen pressure of one atmosphere in the presence of a 10% Pd-C (175 mg.). The reaction was completed in 12 hours. The same after-treatment as in Example 1 was followed to give methyl ester of phenylalanylvaline (376 mg., yield: 81.5%) which was an oil. The NMR and IR spectra were completely identical with those of the authentic sample obtained in Example 5.

EXAMPLE 7

According to the same procedure as in Example 1, 1-(1-methoxycarbonylbenzyl)-3-benzyloxy-4-phenylazetidin-2-one (920 mg.) was subjected to hydrogenolysis at 50° C. in ethanol (10 ml.) under a hydrogen pressure of one atmosphere in the presence of a 10% Pd-C (100 mg.). The reaction was completed in 12 hours. The same after-treatment as in Example 1 was followed to give methyl ester of α-hydroxy-β-phenylpropionylphenylglycine (630 mg., yield: 87.9%), which was an oil. The oily substance is a mixture of two kinds of diastereomers (Diastereomers A and B), which were separated from each other by silica gel chromatography.

Diastereomer A

White crystal, M.P.: 124°–126° C.

NMR (CDCl$_3$): δ 2.83 (quartet, 1H), 2.96 (doublet, 1H), 3.10 (quartet, 1H), 3.625 (singlet, 3H), 4.30 (multiplet, 1H), 5.48 (doublet, 1H), 6.90–7.50 (multiplet, 11H).

IR (KBr disk): 3700–3100 ($v_{OH}$ and $v_{NH}$), 1740 ($v_{C=O}$), 1660 (amide I), 1540 (amide II)cm$^{-1}$.

Diastereomer B

White crystal, M.P.: 115°–117° C.

NMR (CDCl$_3$): δ 2.79 (quartet, 1H), 3.00 (broad doublet, 1H), 3.15 (quartet, 1H), 3.62 (singlet, 3H), 4.16 (multiplet, 1H), 5.47 (doublet, 1H), 6.0–7.6 (multiplet, 11H).

IR (KBr disk): 3700–3100 ($v_{OH}$ and $v_{NH}$), 1740 ($v_{C=O}$), 1660 (amide I), 1520 (amide II)cm$^{-1}$.

EXAMPLE 8

According to the same procedure as in Example 1, 1-(1-methoxycarbonyl-2-methylpropyl)-3-benzyloxy-4-phenylazetidin-2-one (560 mg.) was subjected to hydrogenolysis at room temperature in ethanol (30 ml.) under a hydrogen pressure of one atmosphere in the presence of a 10% Pd-C (170 mg.). The reaction was completed in 38 hours. The same after-treatment as in Example 1 was followed to give methyl ester of α-hydroxy-β-phenylpropionylvaline (400 mg., yield: 93.7%), which was an oil.

NMR (CDCl$_3$): δ0.70–1.04 (multiplet, 6H), 2.09 (multiplet, 1H), 2.70–3.40 (multiplet, 3H), 3.67 (singlet, 3H), 4.12–4.60 (multiplet, 2H), 6.80–7.20 (multiplet, 1H), 7.25 (broad singlet, 5H).

IR (KBr): 3600–3150 ($v_{OH}$ and $v_{NH}$), 1740 ($v_{C=O}$), 1655 (amide I), 1520 (amide II)cm$^{-1}$.

EXAMPLE 9

According to the same procedure as in Example 1, Diastereomer A (700 mg.) of 1-(1-methoxycarbonylethyl)-3-benzyloxy-4-phenylazetidin-2-one, which had been obtained in Example 5, was subjected to hydrogenolysis at room temperature in ethanol (40 ml.) under a hydrogen pressure of one atmosphere in the presence of a 10% Pd-C (220 mg.). The reaction was completed in 12 hours. The same after-treatment as in Example 1 was followed to give methyl ester of α-hydroxy-β-phenylpropionylalanine (468 mg., yield: 90.5%), which was an oil.

NMR (CDCl$_3$): δ1.36 (doublet, 3H), 2.82 (quartet, 1H), 2.96 (doublet, 1H), 3.19 (quartet, 1H), 3.69 (singlet, 3H), 4.24 (multiplet, 1H), 4.52 (quintet, 1H), 6.99 (broad doublet, 1H), 7.25 (singlet, 5H).

IR (KBr): 3375 ($v_{OH}$ and $v_{NH}$), 1740 ($v_{C=O}$), 1645 (amide I), 1520 (amide II)cm$^{-1}$.

EXAMPLE 10

According to the same procedure as in Example 1, 1-(1-methoxycarbonyl-2-phenylethyl)-3-benzyloxy-4-phenylazetidin-2-one (1.0 g.) was subjected to hydrogenolysis at 50° C. in methanol (50 ml.) under a hydrogen pressure of one atmosphere in the presence of a 10% Pd-C (255 mg.). The reaction was completed in 48 hours. The same after-treatment as in Example 1 was followed to give methyl ester of α-hydroxy-β-phenylpropionylphenylalanine (784 mg., yield: 100%), which was an oil.

NMR (CDCl$_3$): δ2.40–3.26 (multiplet, 4H), 3.36 (broad doublet, 1H), 3.64 (singlet, 3H), 4.20 (multiplet, 1H), 4.82 (multiplet, 1H), 6.60–7.60 (multiplet, 11H).

IR (KBr): 3400 ($v_{OH}$ and $v_{NH}$), 1740 ($v_{C=O}$), 1660 (amide I), 1510 (amide II)cm$^{-1}$.

EXAMPLE 11

According to the same procedure as in Example 1, 1-(1-methoxycarbonylethyl)-3-hydroxy-4-phenylazetidin-2-one (513 mg.), which had been obtained in Referential Example 6, was subjected to hydrogenolysis at 50° C. in ethanol under a hydrogen pressure of one atmosphere in the presence of a 10% Pd-C (220 mg.).

The reaction was completed in 12 hours. The same after-treatment as in Example 1 was followed to give methyl ester of α-hydroxy-β-phenylpropionylalanine (475 mg., yield: 91.9%), which was an oil. The NMR and IR spectra were completely identical with those of the authentic sample obtained in Example 9.

EXAMPLE 12

After a hydrogen chloride gas was blown into 20 ml. of a methanolic solution of 1-(1-methoxycarbonylethyl)-3-amino-4-phenylazetidin-2-one (170 mg.) for 5 minutes under ice-cooling, the solvent was removed by distillation using a rotary evaporator to obtain 170 mg. (yield: 100%) of a β-lactam hydrochloride. The thus obtained hydrochloride was subjected to hydrogenolysis at 50° C. in methanol (20 ml.) under a hydrogen pressure of one atmosphere in the presence of a 10% Pd-C (130 mg.) according to the same procedure as in Example 1. The reaction was completed in 24 hours. After the catalyst was removed by filtration using a glass-filter No. G4, the solvent was removed by distillation using a rotary evaporator to obtain 200 mg. of a residue. To the thus obtained residue was added 20 ml. of chloroform and an ammonia gas was blown thereinto over 5 minutes under ice-cooling. The resulting solution was washed with water and then dried over anhydrous magnesium sulfate. Upon removal of the solvent by an evaporator and then under reduced pressure, 170 mg. of an oil was obtained. The resulting oil was further purified by silica gel column chromatography to give 150 mg. (yield: 87.6%) of methyl ester of phenylalanylalanine, which was an oil.

NMR (CDCl$_3$): δ1.38 (doublet, 3H), 1.40 (singlet, 2H), 2.66 (triplet, 1H), 3.25 (triplet, 1H), 3.57 (triplet, 1H), 3.71 (singlet, 3H), 4.56 (quintet, 1H), 7.26 (broad singlet, 5H), 7.55 (broad doublet).

IR (KBr): 3325 ($v_{NH_2}$ and $v_{NH}$), 1742 ($v_{C=O}$), 1660 (amide I), 1500 (amide II) cm$^{-1}$.

EXAMPLE 13

After 1-(1(S)-t-butoxycarbonylethyl)-3(S)-azido-4(R)-phenylazetidin-2-one (200 mg., 0.63 mmol) was hydrogenated in 50 ml. of ethanol under ambient pressure at room temperature for 4 hours, using a 10% Pd-C (200 mg.) as a catalyst, 1 normal (1 N) hydrochloric acid (0.76 ml.) was added thereto. Then, the hydrogenation under ambient pressure was continued further for 15 hours at 50° C. to give quantitatively hydrochloride of t-butyl ester of L-phenylalanyl-L-alanine.

$[\alpha]_D^{20}$: −17.2° (C=1.09, MeOH)
IR (KBr): 3210, 1740, 1670, 1560, 1150 cm$^{-1}$.

The thus obtained product was identical with a dipeptide standard sample (authentic sample) which had been synthesized by an alternative method.

EXAMPLE 14

According to the same procedure as in Example 13 except that 1-(1(S)-t-butoxycarbonylethyl)-3(R)-azido-4(S)-phenylazetidin-2-one (200 mg., 0.63 mmol) was used as a starting material, hydrochloride of t-butyl ester of D-phenylalanyl-L-alanine was obtained quantitatively.

$[\alpha]_D^{20}$: −61.5° (C=1.01, MeOH)
IR (KBr): 3210, 1740, 1680, 1560, 1150 cm$^{-1}$.

The thus obtained product was identical with a dipeptide standard sample (authentic sample) which had been synthesized by an alternative method.

EXAMPLE 15

After 1-(1(S)-t-butoxycarbonylethyl)-3(S)-azido-4(R)-phenylazetidin-2-one (300 mg., 0.95 mmol) was stirred in trifluoroacetic acid (2 ml.) at room temperature for 15 hours, the solvent was removed by distillation under reduced pressure. The thus obtained oil (360 mg.) was hydrogenated in 25 ml. of ethanol at 50° C. for 15 hours under ambient pressure using a 10% Pd-C (300 mg.) as a catalyst to give trifluoroacetic acid salt of L-phenylalanyl-L-alanine (311 mg., yield: 94%).

$[\alpha]_D^{20}$: +11.3° (C=1.00, MeOH)
IR (KBr): 3250, 1730, 1680, 1200, 1140 cm$^{-1}$.

EXAMPLE 16

According to the same procedure as in Example 15 except that 1-(1(S)-t-butoxycarbonylethyl)-3(R)-azido-4(S)-phenylazetidin-2-one (300 mg., 0.95 mmol) was used as a starting material, trifluoroacetic acid salt of D-phenylalanyl-L-alanine (316 mg., yield: 95%) was obtained.

$[\alpha]_D^{20}$: −16.6° (C=1.01, MeOH)
IR (KBr): 3250, 1730, 1680, 1200, 1140 cm$^{-1}$.

EXAMPLE 17

According to the same procedure as in Example 13 except that 1-(1(S)-t-butoxycarbonyl-3-methylbutyl)-3-azido-4-phenylazetidin-2-one (358 mg., 1.0 mmol) was used as a starting material, hydrochloride of t-butyl ester of D/L-phenylalanyl-L-leucine was obtained in a quantitative yield.

IR (KBr): 3210, 1740, 1680, 1560, 1150 cm$^{-1}$.

EXAMPLE 18

According to the same procedure as in Example 13 except that 1-(1(S)-t-butoxycarbonyl-3-methylbutyl)-3-azido-4-(4-fluorophenyl)azetidin-2-one (376 mg., 1.0 mmol), hydrochloride of t-butyl ester of D/L-p-fluorophenylalanyl-L-leucine was obtained in a quantitative yield.

IR (KBr): 3210, 1740, 1680, 1560, 1150 cm$^{-1}$.

EXAMPLE 19

1-(1(S)-Benzyloxycarbonyl-3-methylbutyl)-3-azido-4-phenylazetidin-2-one (200 mg., 0.51 mmol) was hydrogenated in 10 ml. of ethanol at 50° C. for 19 hours under ambient pressure using a 10% Pd-C (270 mg.) as a catalyst to give D/L-phenylalanyl-L-leucine quantitatively.

IR (KBr): 3210, 1670, 1580 cm$^{-1}$.

We claim:
1. A process for the preparation of a dipeptide represented by the formula

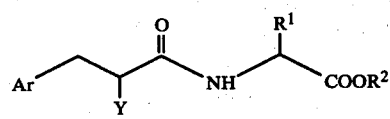

wherein Ar represents an aromatic group; R$^1$ represents a hydrogen atom, an alkyl group or an aryl group; R$^2$ represents a hydrogen atom, an alkyl group or an aromatic group; Y represents a hydroxy group, an amino group or an acylamino group,
which comprises subjecting a β-lactam compound represented by the formula

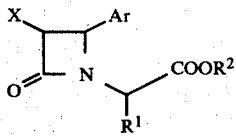

wherein Ar, $R^1$ and $R_2$ have the same meanings as defined above, and X represents a hydroxy group, an amino group or an acylamino group, an azido group or benzyloxy group,
to hydrogenolysis in the presence of a catalyst consisting essentially of palladium.

2. A process according to claim 1 wherein the amount of the catalyst to be used ranges from 0.1 to 100 mole % in terms of the palladium atom, based on the β-lactam compound.

3. A process according to claim 2 wherein the amount of the catalyst to be used ranges from 1 to 50 mole % in terms of the palladium atom, based on the β-lactam compound.

4. A process according to claim 1 wherein the hydrogenolysis is carried out at a temperature of 0° to 150° C.

5. A process according to claim 4 wherein the hydrogenolysis is carried out at a temperature of from room temperature to 100° C.

6. A process according to claim 1 wherein the hydrogenolysis is carried out in a solvent.

7. A process according to claim 1, wherein the group represented by Ar comprises phenyl, naphthyl, pyridyl, pyrrolyl, furyl, indolyl or imidazolyl.

8. A process according to claim 1, wherein $R^1$ or $R^2$ comprises methyl, ethyl, propyl, isopropyl, butyl, isobutyl, sec-butyl, tert-butyl, phenyl, naphthyl, pyridyl, pyrrolyl, furyl, indolyl or imidazolyl.

9. A process according to claim 1, wherein the acylamino group represented by X or Y comprises acetylamino, azidoacetylamino, chloroacetylamino, trichloroacetylamino, trifluoroacetylamino, benzylamino, t-butyoxycarbonylamino, benzyloxycarbonylamino or p-nitrobenzyloxycarbonylamino.

10. A process according to claim 1, wherein the β-lactam compound comprises
1-(1-Methoxycarbonylbenzyl)-3-azido-4-phenylazetidin-2-one,
1-(1-Ethoxycarbonylbenzyl)-3-amino-4-phenylazetidin-2-one,
1-(1-Ethoxycarbonylbenzyl)-3-acetylamino-4-phenylazetidin-2-one,
1-(1-Methoxycarbonylbenzyl)-3-benzyloxy-4-phenylazetidin-2-one,
1-(1-Methoxycarbonylbenzyl)-3-hydroxy-4-phenylazetidin-2-one,
1-(1-Methoxycarbonyl-2-methylpropyl)-3-azido-4-phenylazetidin-2-one,
1-(1-Ethoxycarbonyl-2-methylpropyl)-3-amino-4-phenylazetidin-2-one,
1-(1-Methoxycarbonyl-2-methylpropyl)-3-acetylamino-4-phenylazetidin-2-one,
1-(1-Ethoxycarbonyl-2-methylpropyl)-3-benzyloxy-4-phenylazetidin-2-one,
1-(1-Methoxycarbonyl-2-methylpropyl)-3-hydroxy-4-phenylazetidin-2-one,
1-(1-Methoxycarbonylethyl)-3-azido-2-phenylazetidin-2-one,
1-(1-Methoxycarbonylethyl)-3-amino-4-phenylazetidin-2-one,
1-(1-Ethoxycarbonyl)-3-acetylamino-4-phenylazetidin-2-one,
1-(1-Methoxycarbonylethyl)-3-benzyloxy-4-phenylazetidin-2-one,
1-(1-Methoxycarbonylethyl)-3-hydroxy-4-phenylazetidin-2-one,
1-(1-Methoxycarbonyl-2-phneylethyl)-3-azido-4-phenylazetidin-2-one,
1-(1-Methoxycarbonyl-2-phenylethyl)-3-amino-4-phenylazetidin-2-one,
1-(1-Methoxycarbonyl-2-phenylethyl)-3-acetylamino-4-phenylazetidin-2-one,
1-(1-Methoxycarbonyl-2-phenylethyl)-3-benzyloxy-4-phenylazetidin-2-one,
1-(1-Methoxycarbonyl-2-phenylethyl)-3-hydroxy-4-phenylazetidin-2-one,
1-(1-Methoxycarbonyl-3-methylthiopropyl)-3-azido-4-phenylazetidin-2-one,
1-(1-Methoxycarbonyl-3-methylthiopropyl)-3-amino-4-phenylazetidin-2-one,
1-(1-Methoxycarbonyl-3-methylthiopropyl)-3-acetylamino-4-phenylazetidin-2-one,
1-(1-Methoxycarbonyl-3-methylthiopropyl)-3-benzyloxy-4-phenylazetidin-2-one,
1-(1-Ethoxycarbonyl-3-methylthipropyl)-3-hydroxy-4-phenylazetidin-2-one,
1-(1-Methoxycarbonylbenzyl)-3-azido-4-(p-benzyloxycarbonyloxyphenyl)azetidin-2-one,
1-(1-Methoxycarbonylbenzyl)-3-azido-(3,4-dibenzyloxyphenyl)azetidin-2-one,
1-(1-Methoxycarbonyl-2methylpropyl)-2-amino-4-(p-benzyloxyphenyl)azetidin-2-one,
1-Ethoxycarbonylmethyl-3-azido-4-phenylazetidin-2-one,
1-(1-Methoxycarbonylethyl)-3-azido-(3,4-bisbenzyloxycarbonyloxyphenyl)azetidin-2-one,
1-Methoxycarbonylmethyl-3-azido-4-(p-t-butoxycarbonyloxyphenyl)-azetidin-2-one,
1-(Methoxycarbonyl-p-benzyloxyphenylmethyl)-3-azido-4-phenylazetidin-2-one,
1-(1-t-Butoxycarbonylethyl)-3-azido-4-phenylazetidin-2-one,
1-(1-t-Butoxycarbonylmethyl)-3-amino-4-(p-benzyloxyphenyl)azetidin-2-one,
1-(1-Benzyloxycarbonyl-2-phenylethyl)-3-azido-4-phenylazetidin-2-one, or
1-(1-Benzyloxycarbonyl-2-methylpropyl)-3-trifluoroacetylamino-4-(p-benzyloxycarbonyloxyphenyl)azetidin-2-one.

11. A process according to claim 1, wherein the palladium catalyst comprises Pd Black (palladium black), Pd-C (palladium on carbon), palladium hydroxide (Pd(OH)$_2$), palladium oxide (PdO) or palladium chloride (PdCl$_2$).

12. A process according to claim 6, wherein the solvent comprises an alcohol, a halogentated aliphatic hydrocarbon, an aromatic hydrocarbon, an ether or an aprotic polar solvent.

13. A process according to claim 12, wherein the solvent comprises methanol, ethanol, methylene chloride, chloroform, benzene, toluene, tetrhydrofuran, acetonitrile or dimethylformamide.

* * * * *